US012569396B2

(12) United States Patent
Berry

(10) Patent No.: US 12,569,396 B2
(45) Date of Patent: Mar. 10, 2026

(54) HEATED MASSAGING BRACE

(71) Applicant: Pamela Berry, Greenville, SC (US)

(72) Inventor: Pamela Berry, Greenville, SC (US)

( * ) Notice: Subject to any disclaimer, the term of this patent is extended or adjusted under 35 U.S.C. 154(b) by 0 days.

(21) Appl. No.: 16/790,029

(22) Filed: Feb. 13, 2020

(65) Prior Publication Data

US 2020/0253815 A1      Aug. 13, 2020

Related U.S. Application Data

(60) Provisional application No. 62/805,230, filed on Feb. 13, 2019.

(51) Int. Cl.
*A61H 15/02* (2006.01)
*A61F 5/01* (2006.01)
*A61H 1/00* (2006.01)

(52) U.S. Cl.
CPC ........... *A61H 15/02* (2013.01); *A61F 5/0109* (2013.01); *A61H 1/00* (2013.01); *A61H 2201/0207* (2013.01); *A61H 2201/50* (2013.01); *A61H 2201/5082* (2013.01); *A61H 2205/102* (2013.01)

(58) Field of Classification Search
None
See application file for complete search history.

(56) References Cited

U.S. PATENT DOCUMENTS

| | | | | |
|---|---|---|---|---|
| 5,005,565 | A * | 4/1991 | Fratesi | A61F 5/0125 |
| | | | | 2/22 |
| 6,649,886 | B1 * | 11/2003 | Kleshchik | H05B 3/347 |
| | | | | 219/217 |
| 7,693,580 | B2 | 4/2010 | Docherty et al. | |
| 8,523,793 | B1 * | 9/2013 | Waldon, Sr. | A61H 23/02 |
| | | | | 601/46 |
| 10,874,579 | B1 * | 12/2020 | Rembert | A61H 9/0078 |
| 10,932,939 | B1 * | 3/2021 | Pahls | A61F 5/0123 |
| 2004/0260211 | A1 * | 12/2004 | Maalouf | A61H 23/02 |
| | | | | 601/70 |
| 2005/0043655 | A1 | 2/2005 | Schenck | |
| 2007/0255187 | A1 | 11/2007 | Branch | |
| 2008/0139985 | A1 * | 6/2008 | Gilmour | A61F 5/0123 |
| | | | | 602/26 |
| 2008/0262393 | A1 | 10/2008 | Docherty et al. | |
| 2010/0249637 | A1 * | 9/2010 | Walter | A61H 23/02 |
| | | | | 600/544 |
| 2012/0157902 | A1 * | 6/2012 | Castillo | A61F 5/0123 |
| | | | | 602/26 |
| 2013/0178772 | A1 * | 7/2013 | Oaks | A61F 5/0123 |
| | | | | 602/26 |

(Continued)

*Primary Examiner* — Brandy S Lee
*Assistant Examiner* — Tina Zhang
(74) *Attorney, Agent, or Firm* — Boudwin Intellectual Property Law, LLC; Daniel Boudwin

(57) ABSTRACT

A heated massaging joint brace comprising a brace structure and a first material. A plurality of massaging elements are disposed on an interior of the first material. A heating element is further disposed on the interior of the first material. A power source is operably coupled to the heating element and the plurality of massaging elements. A controller is disposed on an exterior of the brace structure. The controller can control the speed of the massaging elements and the heat of the heating element. The heated massaging brace can be attached to a wearer to heat and massage the area covered by the brace.

1 Claim, 5 Drawing Sheets

(56)  References Cited

U.S. PATENT DOCUMENTS

| | | | |
|---|---|---|---|
| 2014/0188025 A1* | 7/2014 | Aziz | A61F 5/0106 |
| | | | 602/5 |
| 2014/0277220 A1 | 9/2014 | Brennan et al. | |
| 2016/0136033 A1* | 5/2016 | Johnston | A61H 7/007 |
| | | | 601/129 |
| 2016/0331631 A1* | 11/2016 | Odi | A61H 23/02 |
| 2017/0007487 A1* | 1/2017 | Sun | A61B 5/224 |
| 2018/0228689 A1* | 8/2018 | Lach | A61H 39/007 |
| 2018/0344564 A1* | 12/2018 | Reiniger | A61H 7/004 |
| 2019/0015289 A1* | 1/2019 | Grimoldby | A61F 5/34 |
| 2020/0188154 A1* | 6/2020 | Hsu | A61H 7/004 |

* cited by examiner

501

502

HEATED MASSAGING BRACE

CROSS REFERENCE TO RELATED APPLICATIONS

This application claims the benefit of U.S. Provisional Application No. 62/805,230 filed on Feb. 13, 2019. The above identified patent application is herein incorporated by reference in its entirety to provide continuity of disclosure.

BACKGROUND OF THE INVENTION

The present invention relates to a joint brace with an incorporated massager and warming device. More particularly, the present invention provides a heated and massaging brace that allows a user to heat and massage an area in order to expedite healing.

People regularly become injured or require surgery to correct a torn ligament or have a joint replaced. Many such injuries or surgeries require a significant amount of time to heal. Many times, a brace is required to keep the injured or recently repaired ligament in a specific position for proper healing. When wearing a brace, the brace can often become uncomfortable and cause irritation and discomfort. It can be difficult to alleviate the irritation or discomfort without taking the brace off. This may not be possible.

Further, when recovering it is usually recommended to heat the area and perform massages of the area. Many medical professionals recommend heating an area after surgery or injury to promote healing. It can be difficult to heat an area that is covered by a brace. Further, if a brace is placed too tightly on a body part, it can be difficult to ensure proper blood circulation. A massage can help restore blood flow to the respective area. It can be extremely difficult to ensure proper blood flow and still have a brace applied with the proper tightness.

Consequently, there is a need in for an improvement in the art of joint braces and warming elements. The present invention substantially diverges in design elements from the known art while at the same time solves a problem many people face when recovering from injury or surgery. In this regard the present invention substantially fulfills these needs.

SUMMARY OF THE INVENTION

The present invention provides a heating massaging brace wherein the same can be utilized for providing convenience for the user when supporting a joint to properly heal. The heated massaging brace comprises a brace structure having a first material and at least one brace attached thereto, wherein a plurality of heating elements are disposed on an interior of the brace structure. The plurality of heating elements are disposed along the length of the brace. A plurality of massaging elements are disposed on the interior of the brace structure. The plurality of massaging elements are configured to be heated.

Another object of the heated massaging brace is to further include massaging elements that are vibrators.

Another object of the heated massaging brace is to further include massaging elements that are rollers.

Another object of the heated massaging brace is to further include a second material that provides a layer in between a person's skin and the at least one heating element and the plurality of massaging elements.

Another object of the heated massaging brace is to further include a controller located on an exterior of the brace.

Another object of the heated massaging brace is to further allow the controller controls the temperature of the at least one heating element.

Another object of the heated massaging brace is to further allow the controller controls the speed of the plurality of massaging elements.

Another object of the heated massaging brace is to further include a power source.

Another object of the heated massaging brace is to further include a rechargeable battery.

Other objects, features and advantages of the present invention will become apparent from the following detailed description taken in conjunction with the accompanying drawings.

BRIEF DESCRIPTION OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
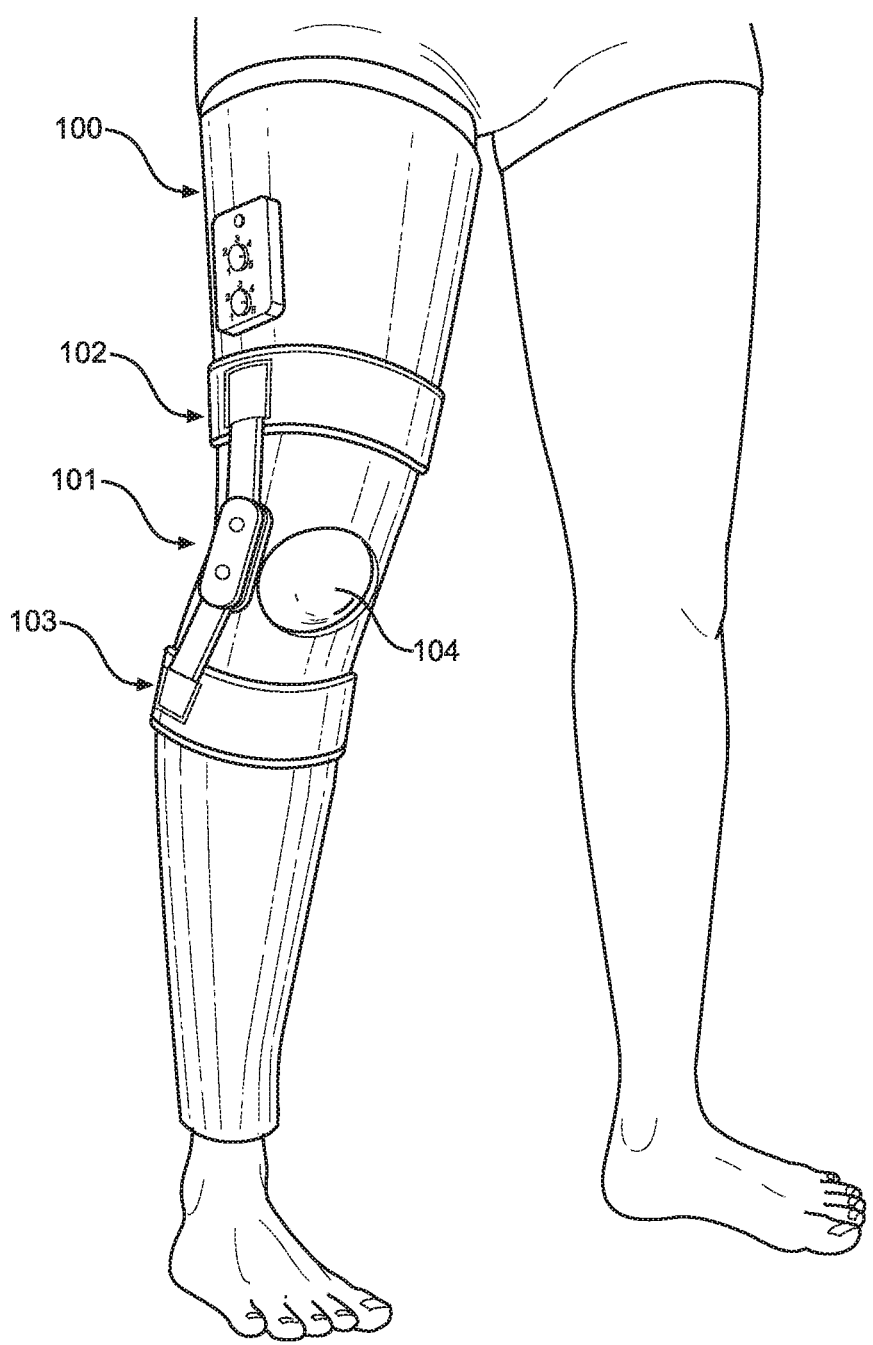
FIG. 1 shows a perspective view of an embodiment of the heating massage brace on a knee.

Reference is made herein to the attached drawings. Like reference numerals are used throughout the drawings to depict like or similar elements of the heating massage brace. For the purposes of presenting a brief and clear description of the present invention, a preferred embodiment will be discussed as used for the heating massage brace. The figures are intended for representative purposes only and should not be considered to be limiting in any respect.

Referring now to FIG. 1, there is shown a perspective view of an embodiment of the heating massage brace on a knee. The heating massage brace includes a body portion 100. The body portion 100 is the section that wraps around the joint and body part to be supported. The body portion 100 comprises a brace structure 101 attached to the outside thereof. In one embodiment, the brace structure 101 is attached to the body portion 100 via connectors 102, 103. In one embodiment, the connectors 102, 103 are comprised of a top connector 102 and a lower connector 103. These connectors 102, 103 secure the brace structure 101 in place along the joint. Further, the brace structure 101 will support the body part and the joint. In the shown embodiment, there is a single brace structure 101 on the outside of heating massage brace. In other embodiments, there can be an additional brace structure 101 on the inside of the heating massage brace. In one embodiment, a hole 104 is located in the heating massage brace. This hole 104 can allow part of the body to be placed therein. The hole 104 can allow pressure to be released or to hold a body part in place.

Figure 2:
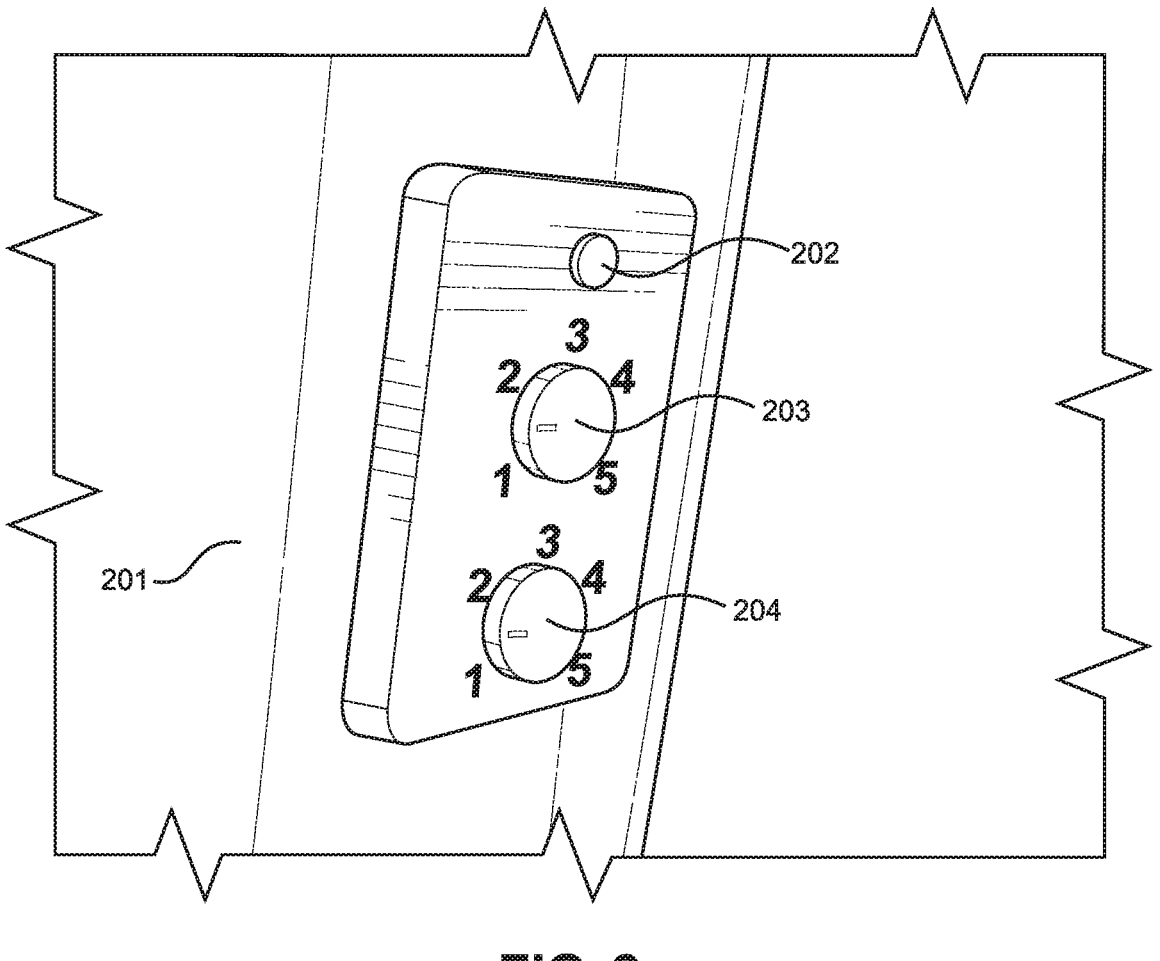
FIG. 2 shows a perspective view of an embodiment of the heating massage brace with a controller attached thereto.

Referring now to FIG. 2, there is shown a perspective view of an embodiment of the heating massage brace with a controller attached thereto. In the illustrated embodiment, a controller 201 is attached to the exterior of the heating massage brace. The controller 201 controls the temperature of the heating elements and speed and depth of the massaging elements. In the shown embodiment, the controller 201 further comprises a power light 202. The power light 202 illuminates when one of features of the heating massage brace is activated. In the shown embodiment, there are two knobs 203 and 204. Each of these knobs 203, 204 can activate one of the features of the heating massaging brace. For example, the top knob 203 can control the temperature of the heating elements, while the bottom knob 204 can control the speed of the massaging element.

Figures 3, 4:
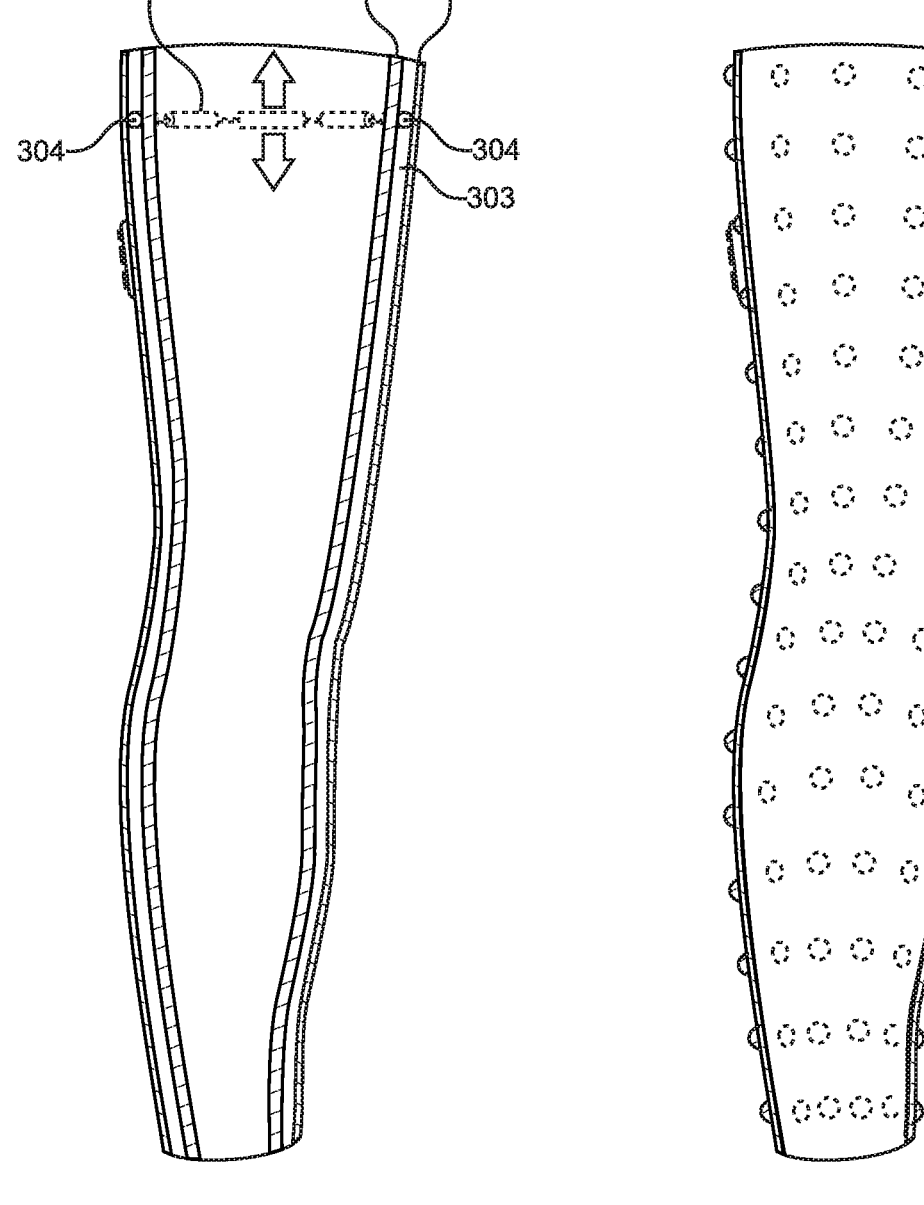
FIG. 3 shows a cross-sectional view of an embodiment of the heating massage brace with rollers.
FIG. 4 shows a cross-sectional view of an embodiment of the heating massage brace having vibrators.

Referring now to FIG. 3, there is shown a cross-sectional view of an embodiment of the heating massage brace with rollers. In one embodiment, the heating massage brace has a plurality of layers. The first layer 301 is the inner most layer. The first layer 301 comprises a material having a quality that will allow it to stick to skin and keep the heating massage brace in place on the body part to be supported. In one embodiment, the first layer 301 is neoprene. The outer layer 302 is a protection layer. In one embodiment, the outer layer 302 is a fabric layer. In one embodiment, the outer layer 302 is a padded layer. In the embodiment of FIG. 3 there is a channel 303. The channel 303 can incorporate a plurality of rollers 304. The plurality of rollers 304 are configured to fit around a body part applying pressure. The plurality of rollers 304 will move up and down the body part as a massaging element when activated. In this embodiment the rollers may be capable of providing a deep tissue massage.

Referring now to FIG. 4, there is shown a cross-sectional view of an embodiment of the heating massage brace having vibrators. In one embodiment, the massaging elements are vibrating elements 401. The vibrating elements 401 are configured to press against the body when the heating massage brace is correctly fitted to the body. In one embodiment, the vibrating balls 401 can also be configured to double as the heating elements. In this embodiment the vibrating feature and the heating feature are still controlled independently of each other.

Figure 5:
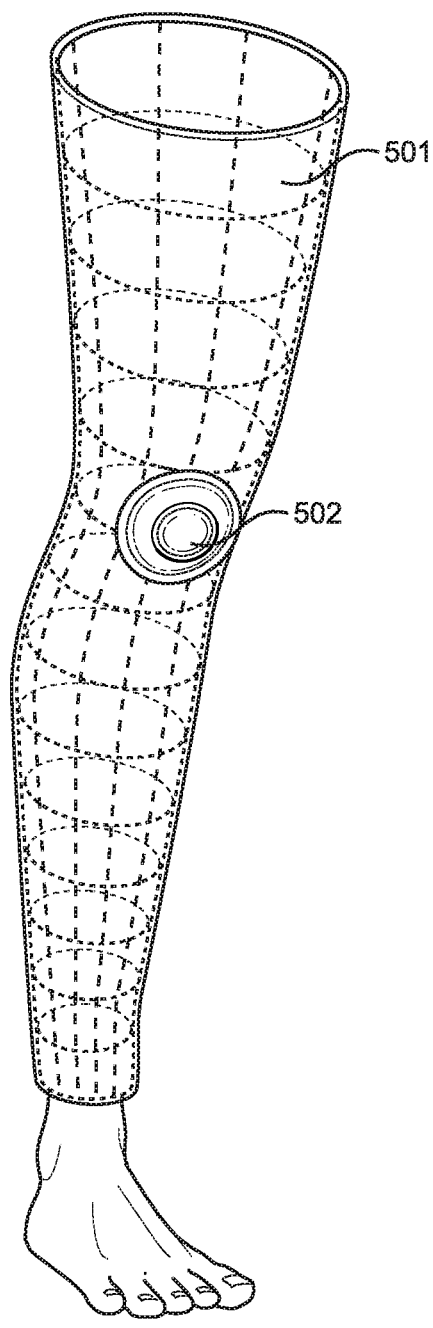
FIG. 5 shows a perspective view of an embodiment of the heating massage brace with heating elements throughout.

Referring now to FIG. 5, there is shown a perspective view of an embodiment of the heating massage brace with heating elements throughout. In one embodiment of the heating massage brace, the heating element is a web of heating elements 501. In one embodiment the web of heating elements 501 are configured to be spread throughout the heating massage brace. In another embodiment the web of heating elements 501 are confined to a specific location of the heating massage brace. This will allow the web of heating elements 501 to be spread throughout the brace independently of the massaging elements. In this embodiment, this can also allow for the heating massage brace to be heated without activating a massaging element. In one embodiment, there is an additional pad 502 placed on the heating massage brace. The additional pad 502 may apply added pressure to an area of the body.

Figure 6:
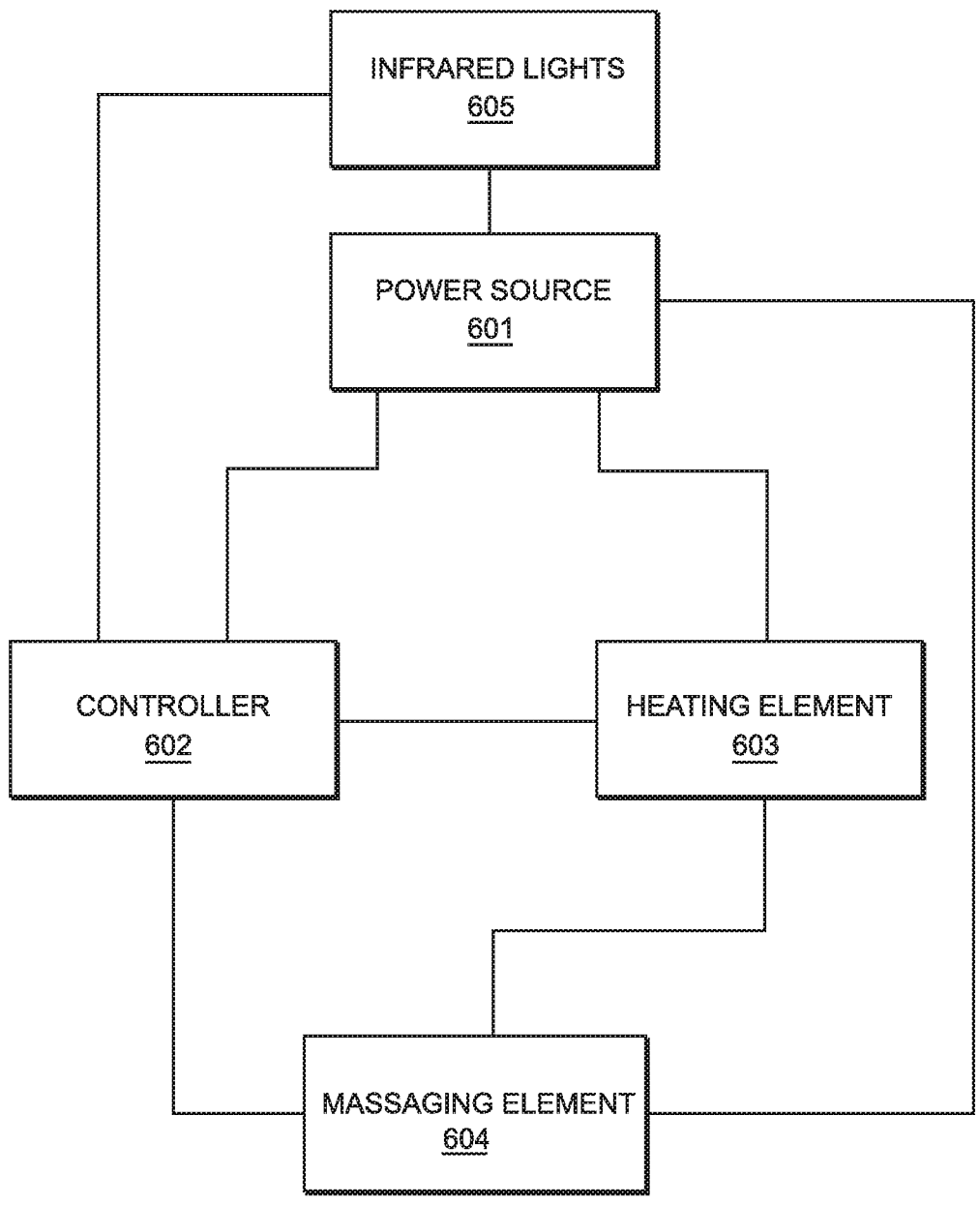
FIG. 6 shows a schematic view of an embodiment of the wiring for the heating massage brace.

Referring now to FIG. 6, there is shown a schematic view of an embodiment of the wiring for the heating massage brace. The heating massage brace has a plurality of elements all connected together. The heating massage brace has a power source 601. In one embodiment, the power source 601 is a battery. In another embodiment, the power source 601 is a wall plug. The power source 601 is connected to the controller 602. The controller 602 controls the massaging and heating strength. The controller 602 is connected to the heating element 603. The heating element 603 is also attached to the power source 601. The controller 602 is operably coupled to the massaging element 604. The massaging element 604 is also coupled to the power source 601.

In one embodiment the brace also includes at least one infrared light 605. The infrared light is configured to shine into the interior of the brace. The infrared light 605 is connected to the controller 602 and the power source 601. In embodiment the controller is further configured to activate the infrared light 605. In another embodiment the infrared light is configured to be activated when the massaging element 604 is activated. In yet a further embodiment the infrared light 605 is configured to be activated when the heating element 603 is activated.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A heated massaging brace, consisting of:

a body portion consisting of a first material defining an open upper end and an open lower end;

wherein the body portion further consists of a second material that is configured to provide a layer in between a person's skin and at least one heating element and a plurality of massaging elements;

wherein the second material consists of a different material than that of the first material;

at least one brace structure attached to the body portion;

further consisting of a controller located on an exterior of the body portion;

wherein the controller consists of a plurality of controls thereon;

wherein a first control of the plurality of controls disposed on the controller consists of a knob configured to selectively adjust a temperature of the at least one heating element between a plurality of preset temperature levels;

wherein a second control of the plurality of controls disposed on the controller consists of a knob configured to selectively adjust a speed of the plurality of massaging elements between a plurality of preset speed levels;

wherein the brace structure consists of a top connector wrapping about a circumference of the body portion adjacent to the open upper end and a lower connector wrapping about a circumference of the body portion adjacent to the open lower end;

wherein the first material consists of a quality that allows the first material to stick to skin;

wherein a first brace extends from the top connector and is hingedly affixed to a second brace extending from the lower connector;

wherein a pocket is disposed on each of the top connector and the lower connector;

wherein a hole is disposed through the body portion along a front side thereof;

wherein a supplemental pad is affixed to the body portion;

wherein the supplemental pad overlies an entirety of the hole;

wherein a proximal end of each of the first brace and the second brace is disposed within each pocket;

the at least one heating element disposed on an interior of the body portion;

wherein at least one heating element is disposed to run the length of the body portion;

wherein the at least one heating element consists of a web of heating lines disposed throughout the body portion;

wherein the web of heating lines include a plurality of circumferential heating lines disposed between the open upper end and the open lower end and a plurality of longitudinal heating lines perpendicularly intersecting the plurality of circumferential heating lines;

wherein the plurality of massaging elements are disposed on the interior of the body portion;

wherein the plurality of massaging elements are configured to be heated;

wherein the massaging elements consist of a plurality of rollers disposed end to end about an entire circumference of the body portion;

wherein the plurality of rollers are configured to selectively travel between the open upper end and the open lower end;

further consisting of at least one infrared light disposed on an interior surface of the body portion;

wherein the at least one infrared light is oriented to emit infrared light into the interior of the body portion; and further consisting of a power source.

\* \* \* \* \*